(12) United States Patent
LaBelle (10) Patent No.: US 8,864,703 B2
(45) Date of Patent: Oct. 21, 2014

(54) DRUG INTRODUCTION AND PLACEMENT SYSTEM

(75) Inventor: Mark D. LaBelle, Chino, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 907 days.

(21) Appl. No.: 12/898,031

(22) Filed: Oct. 5, 2010

(65) Prior Publication Data

US 2012/0083765 A1 Apr. 5, 2012

(51) Int. Cl.
| A61M 29/00 | (2006.01) |
| A61M 25/00 | (2006.01) |
| A61M 31/00 | (2006.01) |
| A61F 9/00 | (2006.01) |
| A61M 37/00 | (2006.01) |

(52) U.S. Cl.
CPC .............. *A61F 9/0017* (2013.01); *A61M 37/00* (2013.01)
USPC ................. 604/96.01; 604/97.01; 604/103.01; 604/103.06

(58) Field of Classification Search
USPC ............ 604/21, 48, 96.01, 521, 97.01, 97.02, 604/99.01, 103.07, 509, 181, 187, 264, 263, 604/171, 294, 192, 103.01, 502, 93.01, 198, 604/57, 59, 60, 288, 891.1, 103.06, 265, 604/289, 298, 300
See application file for complete search history.

(56) References Cited

U.S. PATENT DOCUMENTS

| 4,994,041 | A | * | 2/1991 | Dombrowski et al. | ....... 604/192 |
| 5,469,867 | A | * | 11/1995 | Schmitt | ......................... 128/898 |
| 5,826,584 | A | | 10/1998 | Schmitt | |
| 6,638,292 | B2 | * | 10/2003 | Adams | ........................... 606/192 |
| 7,811,252 | B2 | | 10/2010 | Dacquay et al. | |
| 2005/0182361 | A1 | * | 8/2005 | Lennox | ..................... 604/103.01 |
| 2005/0197667 | A1 | * | 9/2005 | Chan et al. | ..................... 606/194 |
| 2008/0281292 | A1 | | 11/2008 | Hickingbotham et al. | |
| 2009/0030381 | A1 | | 1/2009 | Lind et al. | |
| 2009/0125057 | A1 | | 5/2009 | Cordova | |
| 2010/0016439 | A1 | | 1/2010 | Thomas et al. | |
| 2010/0137785 | A1 | | 6/2010 | Lind | |
| 2010/0174272 | A1 | | 7/2010 | Weiner | |
| 2010/0226962 | A1 | | 9/2010 | Rodstrom et al. | |

OTHER PUBLICATIONS

"http://techdevice.com/" home page—internet archive downloaded from: http://replay.waybackmachine.org/20090303105612/http://techdevice.com/ —dated Mar. 3, 2009.
"http://www.techdevice.com/products/p_b.html"—internet archive downloaded from: http://replay.waybackmachine.org/20090411080415/http://www.techdevice.com/products/p_b.html—dated Apr. 11, 2009.
"http://www.techdevice.com/news.html"—internet archive downloaded from: http://replay.waybackmachine.org/20090322130346/http://www.techdevice.com/news.html—dated Mar. 22, 2009.
http://yulex.com/ —internet archive downloaded from: http://replay.waybackmachine.org/20090227035017/http://yulex.com/—dated Feb. 27, 2009.
Fulzele, Suniket, et al., "Study of Novel Rosin-Based Biomaterials for Pharmaceutical Coating," AAPS PharmSciTech, submitted Sep. 9, 2002, 3(4) Article 31 (http://www.aapspharmscitech.org).
Lind, Casey, et al., "Implantable Punctal Plug," U.S. Appl. No. 12/877,437, filed Sep. 8, 2010, 22 pages.

\* cited by examiner

*Primary Examiner* — Bhisma Mehta
*Assistant Examiner* — Bradley G Thomas, Jr.

(57) ABSTRACT

A drug introduction sleeve is disclosed that includes a selectively expandable body portion. The body portion is defined by a first open end and a second open end. A hollow interior is formed within the body portion. The body portion is selectively expandable from a first unexpanded configuration to a second expanded configuration whereby the volume of the hollow interior is increased when the body portion is expanded to the second expanded configuration, sufficient to temporarily retain a drug bolus.

20 Claims, 8 Drawing Sheets

DRUG INTRODUCTION AND PLACEMENT SYSTEM

TECHNICAL FIELD

The present disclosure generally relates to the field of implantable pharmaceuticals, and methods of drug delivery to the eye. More particularly, the present disclosure relates to a system for introducing and placing a therapeutic compound within the eye in a minimally invasive manner.

BACKGROUND

Glaucoma is the leading cause of blindness worldwide and the most common cause of optic neuropathy. Various forms of glaucoma leads to elevated intraocular pressure, and may also lead to damage to the optic nerve. If glaucoma or ocular hypertension is detected early and treated promptly with medications that effectively reduce elevated intraocular pressure, loss of visual function or its progressive deterioration can generally be ameliorated. Drug therapies that have been proven useful for the reduction of intraocular pressure include both agents that decrease aqueous humor production and agents that increase the outflow facility. Such therapies may be administrated in a number of different ways.

One example of administrating suitable therapies includes topical application to the eye, such as eye drops. However, one of the limitations of topical therapy is inadequate and irregular delivery of the therapeutic agent to the eye. For example, when an eye drop is applied to the eye, a substantial portion of the drop may be lost due to overflow of the lid margin onto the cheek. Moreover, compliance with a necessary drug regime is also always an issue with this method. For example, for some medications, 4 to 5 applications a day are required to achieve therapeutic drug levels.

Other suitable delivery mechanisms for therapeutic devices include injection at the pars plana. However, aside from discomfort for the patient, this method also requires that the patient return monthly. Further, for phase transition type drugs, when the drugs were introduced directly into the eye, there is a risk of inadvertent attachment of the drugs to the delicate tissues within the eye as accurate and optimal placement of the drug is challenging.

Various ocular drug delivery implants have also been employed in an effort to improve and prolong drug delivery. One such example includes a reservoir drug-delivery device. A reservoir drug-delivery device is a device that contains a receptacle or chamber for storing the drug while implanted in the eye. However, reservoir drug devices are difficult to manufacture, difficult to achieve drug content uniformity (i.e., device to device reproducibility, particularly with small ocular devices), and carry the risk of a "dose dump" if they are punctured.

Accordingly, there exists a need for a therapeutic delivery mechanism that allows for ease of introduction and desired placement of a therapeutic agent, while minimizing the incision size to introduce the desired therapeutic agent.

BRIEF SUMMARY

A drug introduction sleeve is disclosed that includes a selectively expandable body portion. The body portion is defined by a first open end and a second open end. A hollow interior is formed within the body portion. The body portion is selectively expandable from a first unexpanded configuration to a second expanded configuration whereby the volume of the hollow interior is increased when the body portion is expanded to the second expanded configuration. A system employing the drug introduction sleeve, as well as a method of introducing a drug into a patient is also disclosed.

BRIEF DESCRIPTION OF THE DRAWINGS

Exemplary embodiments of the present disclosure will now by described by way of example in greater detail with reference to the attached figures, in which.

DETAILED DESCRIPTION

Referring now to the discussion that follows and also to the drawings, illustrative approaches to the disclosed devices and methods are shown in detail. Although the drawings represent some possible approaches, the drawings are not necessarily to scale and certain features may be exaggerated, removed, or partially sectioned to better illustrate and explain the present disclosure. Further the descriptions set forth herein are not intended to be exhaustive or otherwise limit or restrict the claims to the precise forms and configurations shown in the drawings and disclosed in the following detailed description.

Figure 1:
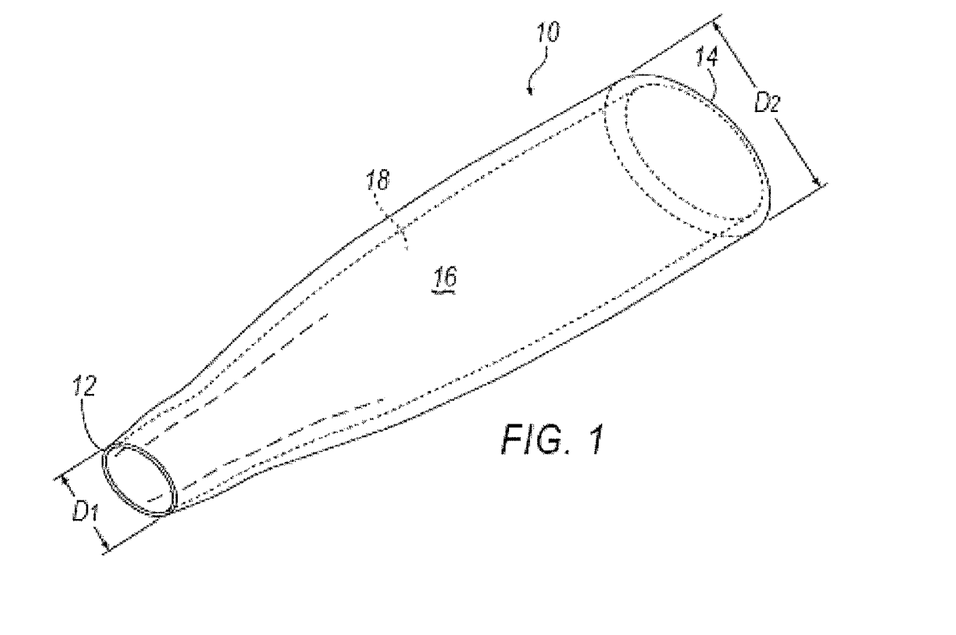
FIG. 1 is a perspective view of a first exemplary arrangement of a selectively expandable sleeve in a first un-expanded configuration.
Figure 2:
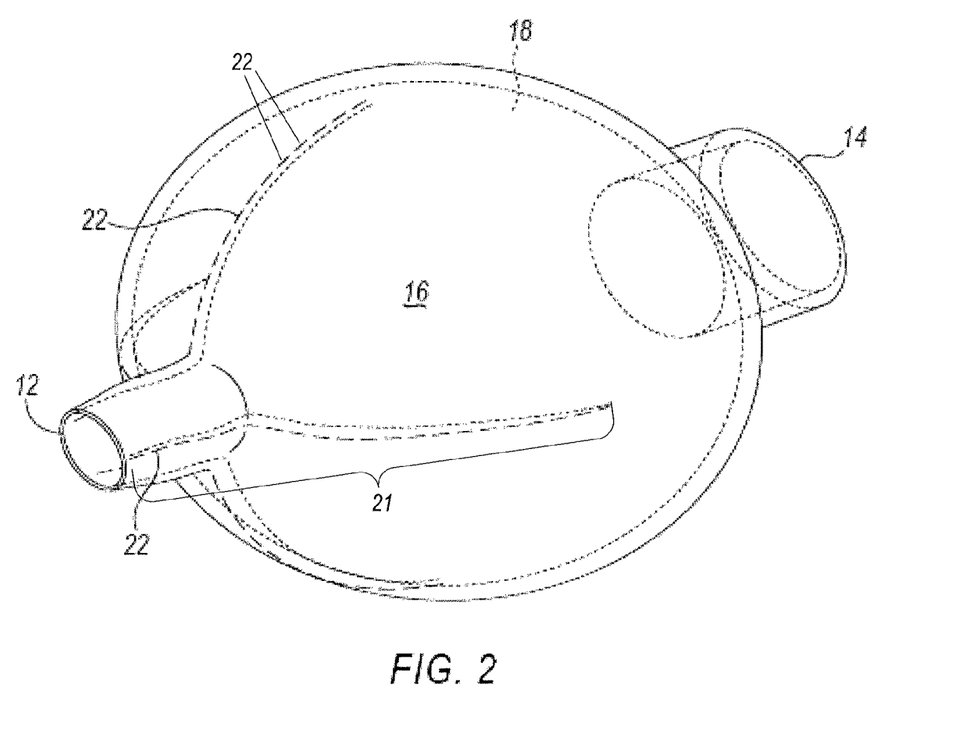
FIG. 2 is a perspective view of the selectively expandable sleeve of FIG. 1 in a second expanded configuration.

Referring to FIGS. 1 and 2, a selectively expandable sleeve 10 is illustrated. Sleeve 10 is defined by a first end 12 and a second end 14, with a body portion 16 spanning therebetween. Body portion 16 defines a hollow interior 18 of sleeve 10. In one exemplary arrangement, first end 12 is configured to taper to a first diameter $D_1$. Second end 14 may be defined by a second diameter $D_2$ that is generally larger than first diameter $D_1$. In another embodiment, first and second diameters $D_1$, $D_2$ may be configured so as to be generally equal.

Body portion 16 is configured so as to permit body portion to expand from a first un-expanded configuration, shown in FIG. 1 to a second expanded configuration, shown in, for example, FIG. 2. In one exemplary arrangement, sleeve 10 is configured with at least one perforation segment 21 defined by perforations 22. As shown in FIGS. 1 and 2, perforations 22 are defined by a predetermined length and are arranged to extend from first end 12 to approximately the center of body portion 16. However, it is understood that the length of perforations 22 may be configured to be longer or shorter than half the length of body portion 16. In one exemplary arrangement, sleeve 10 is configured with a plurality of perforation segments 21. The perforation segments 21 may be arranged equi-distance from one another. Perforations 22 will be explained below in further detail.

Figure 3:
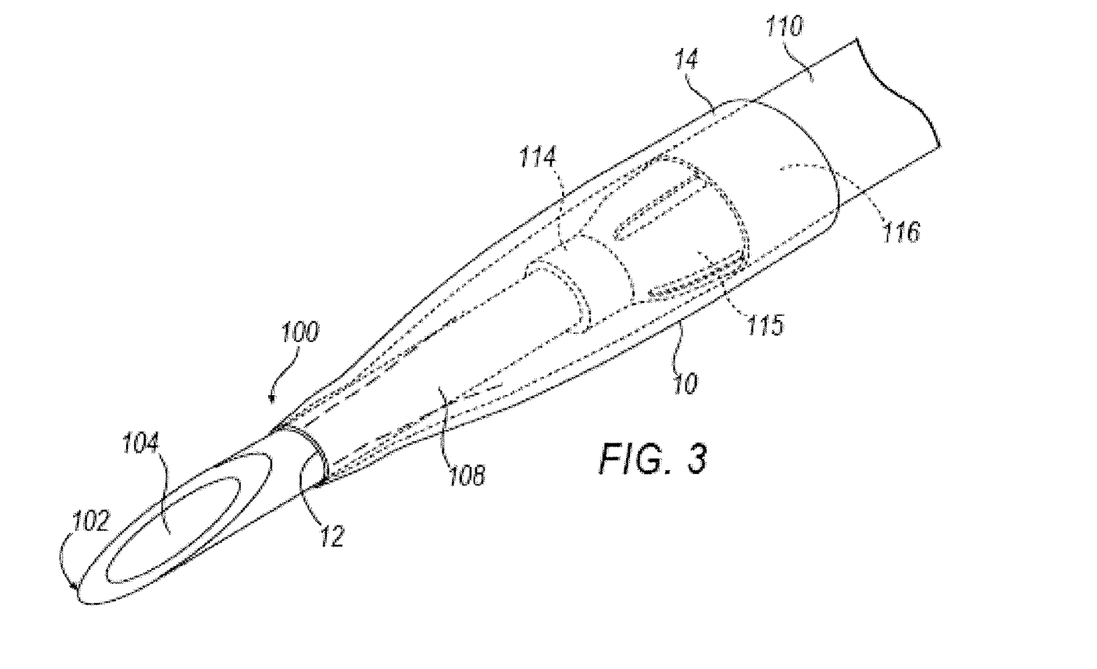
FIG. 3 is a perspective view of the selectively expandable sleeve mounted on a drug introduction tool prior to insertion of the tool into a patient.
Figure 4:
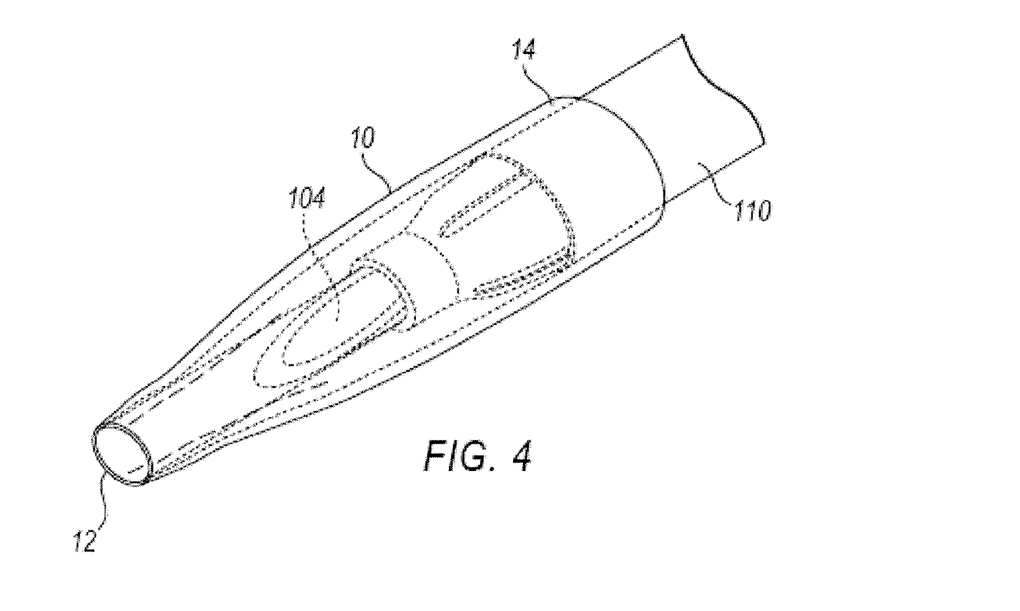
FIG. 4 is a perspective view of the selectively expandable sleeve mounted on the drug introduction tool after insertion into the patient and with a piercing element of the tool at least partially retracted into the sleeve.
Figure 5:
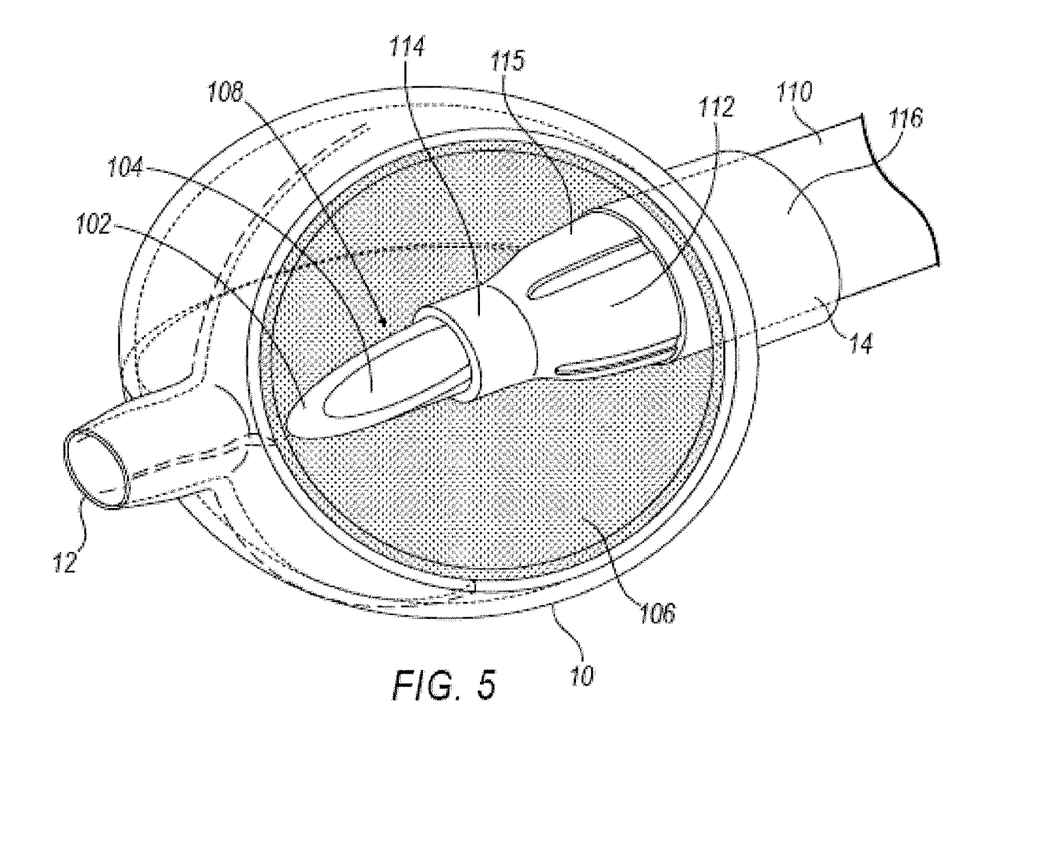
FIG. 5 is a perspective view of the selectively expandable sleeve mounted on the drug introduction tool after introduction of a drug through the tool and into the sleeve.

Referring to FIGS. 3-5, selectively expandable sleeve 10 is shown mounted to a drug introduction tool. In one exemplary arrangement, the drug introduction tool is configured as a hypodermic needle system 100. Needle system 100 includes a needle shaft 108 and a needle housing 110. Needle shaft 108 is defined by a distal piercing end 102 that includes an opening 104 through which a suitable therapeutic drug 106 (shown in FIG. 5) may be dispensed. Needle shaft 108 is slidingly mounted within needle housing 110 such that distal piercing end 102 of needle shaft 108 may be selectively advanced from and retracted into needle housing 110. Needle system 100 is fluidly connected to a suitable drug supply (not shown).

In one embodiment, needle shaft 108 may be provided with a mounting collar 112. As needle housing 110 has a diameter that is larger than a diameter of needle shaft 108, a first end 114 of mounting collar 112 is configured to have a diameter that is smaller than that of needle housing 110, but slightly larger than the diameter of needle shaft 108. A tapered section 115 extends between first end 114 and a distal end 116 of needle housing 110.

Referring to FIG. 3, prior to insertion of distal piercing end 102 into a patient, expandable sleeve 10 is mounted around a portion of needle system 100. More specifically, expandable sleeve 10 is mounted in the first un-expanded configuration such that second end 14 is secured around distal end 116 of needle housing 110. Further, first end 12 is disposed around a portion of needle shaft 108 so as to be spaced away from distal piercing end 102 in the proximal direction.

Once an incision has been made by inserting distal piercing end 102 into the desired location within a patient's eye, needle shaft 108 is retracted into needle housing 110 such that opening 104 of needle shaft 108 is positioned within hollow interior 18 of body portion 16, as shown in FIG. 4. Once opening 104 is positioned within interior 18, a phase transition drug 106 is dispensed through needle shaft 108 and opening 104 to interior 18. Injection of drug 106 causes sleeve 10 to expand into the second expanded configuration shown in FIG. 5. In other words, perforations 22 permit the volume of interior 18 to increase. However, sleeve 10 confines drug 106 within interior 18 as drug 106 is being dispensed so as to form and shape drug 106 into a drug bolus 118 (best seen in FIG. 8) as drug 106 solidifies after dispensing from opening 104. Confining drug 106 in sleeve 10 prevents drug 106 from inadvertently attaching to delicate tissues within the eye when dispensed.

To prevent drug 106 from exiting through first end 12 during the dispensing operation, opening 104 can be positioned closer to second end 14 within interior 18 of sleeve 10.

Due to the properties of the phase transition drug 106, drug bolus 118 will quickly form within interior 18 before drug 106 may exit first end 12.

Figure 6:
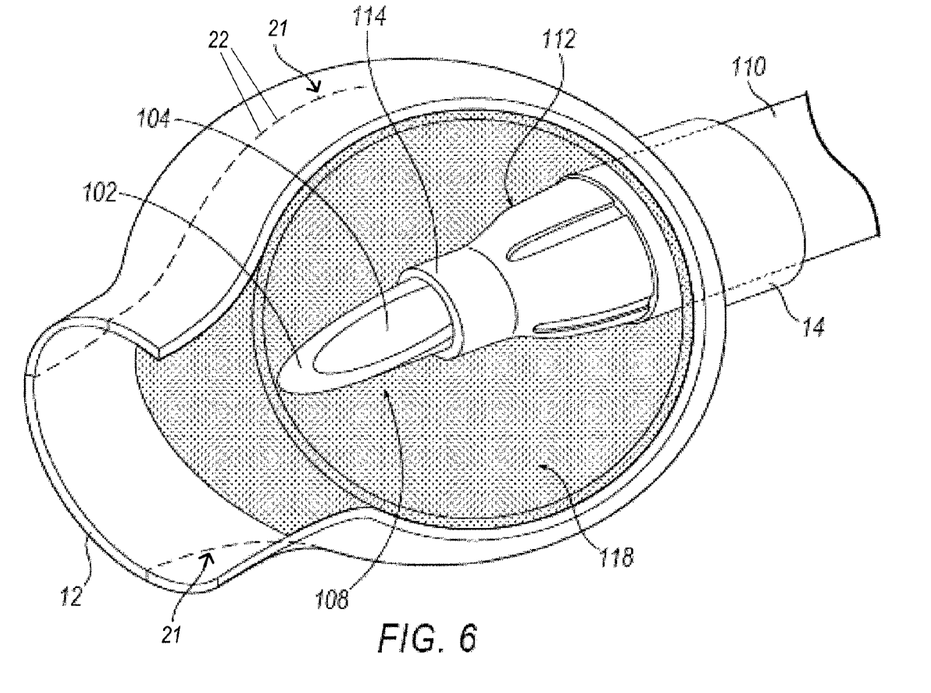
FIG. 6 is a perspective cut-away view of one exemplary arrangement of the selectively expandable sleeve whereby a first end of the sleeve expands during a retraction of the sleeve from the drug bolus formed.
Figure 7:
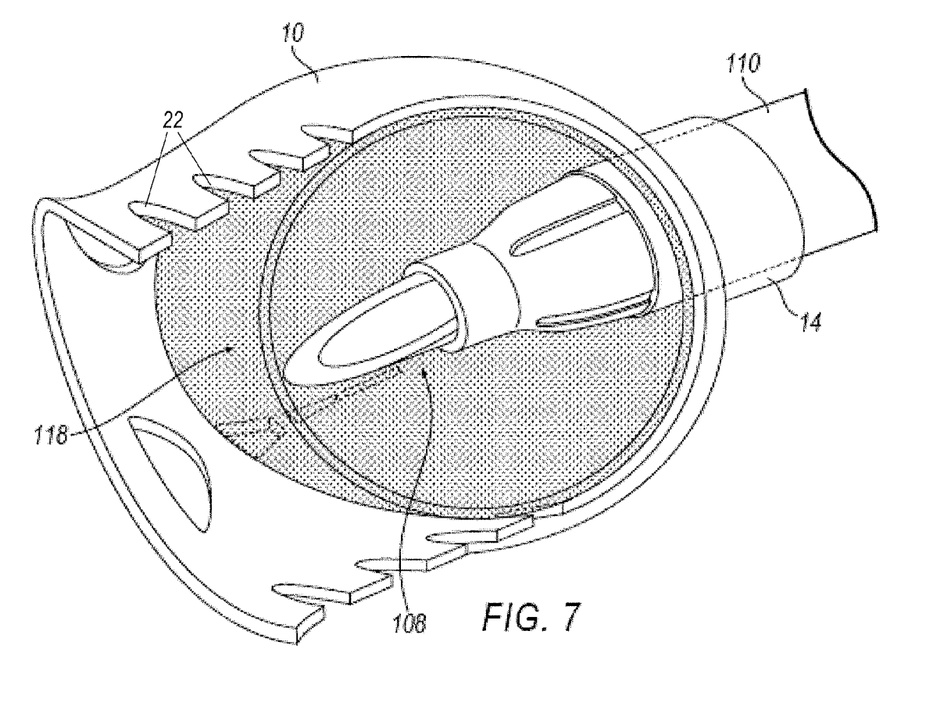
FIG. 7 is a perspective cut-away view of the exemplary arrangement of the selectively expandable sleeve of FIG. 6, illustrating expansion of perforations as the sleeve is retracted over the drug bolus.
Figure 8:
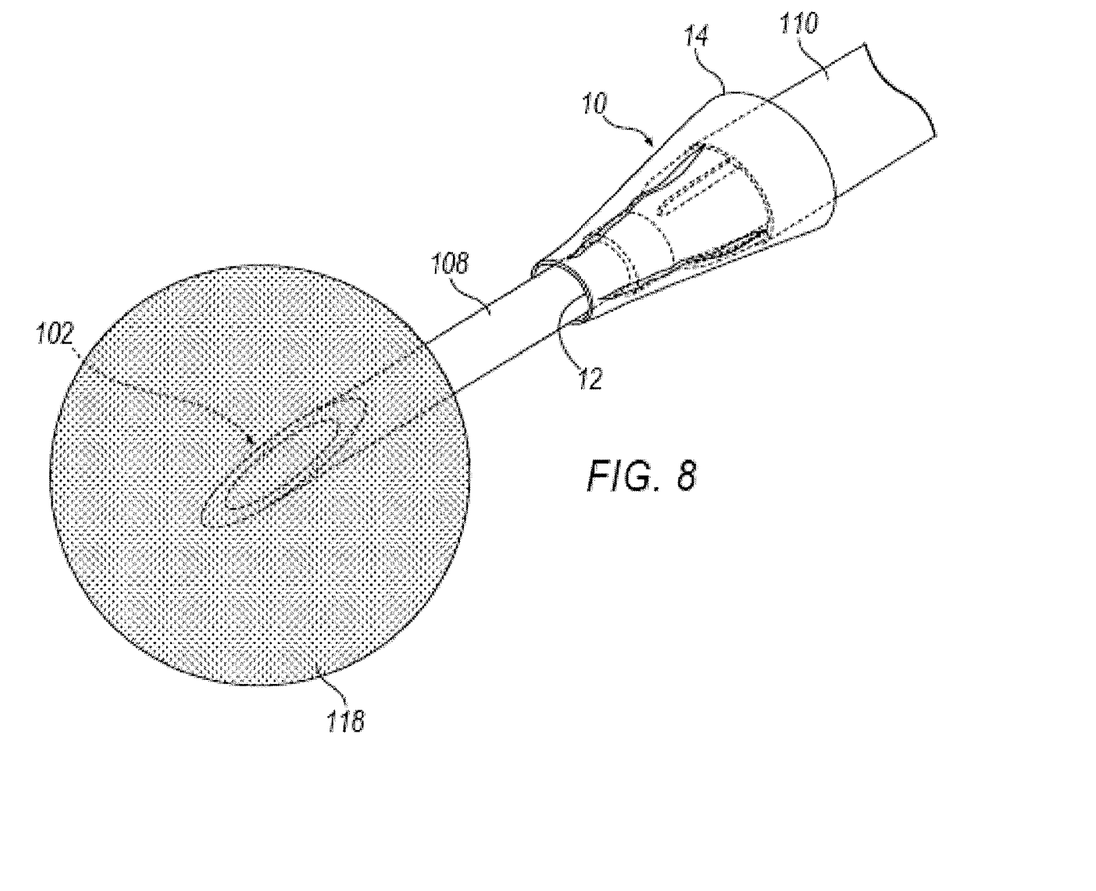
FIG. 8 is a perspective view of the exemplary arrangement of the selectively expandable sleeve of FIGS. 6-7, illustrating the sleeve being withdrawn from the drug, with the piercing element positioned with the drug bolus.

In one exemplary arrangement, referring to FIGS. 6-8, sleeve 10 is constructed of a suitable biocompatible flexible material that is removed from drug bolus 118, as well as the patient, after drug formation and placement. An exemplary material that may be used is non-allergenic surgical latex or a natural rubber material, such as Yulex® Natural Rubber. In this arrangement, second end 14 of sleeve 10 is fixedly secured to needle housing 110. After drug bolus 118 is formed, needle housing 110 is then retracted away from drug bolus 118, while needle shaft 108 remains positioned within the patient. Because second end 14 of sleeve 10 is fixedly secured to needle housing 110, as needle housing 110 is retracted away from the patient, sleeve 10 also retracts. However, as first end 12 of sleeve 10 is smaller than drug bolus 118, sleeve 10 stretches over drug bolus 118, expanding first end 12 (as may be seen in FIG. 6). As first end 12 stretches, perforations 22 stretch apart as shown in FIG. 7 such that sleeve 10 slides over drug bolus 118. In some embodiments, there may be four groups of perforation segments 21 equally spaced on the sleeve diameter (other numbers of perforation segments and other spacings are also possible). While FIG. 7 illustrates four expanded perforations 22 in each perforation segment 21, it is to be understood that each perforation segment 21 may include many perforations 22 as shown in FIG. 2. The perforations 22 may stretch as the sleeve 10 stretches. As shown in FIG. 8, sleeve 10 may completely retract from drug bolus 118. However, because sleeve 10 is constructed of a flexible material, sleeve 10 can easily be compressed and retracted through the small incision required by the needle system 100. Indeed, for eye surgery, the incision may be small enough that sutures are not even required after drug injection. In one exemplary configuration, the incision is between 25-30 GA.

Referring to FIG. 8, after needle housing 110 and sleeve 10 is retracted from drug bolus 118, distal piercing end 102 of needle shaft 108 remains within drug bolus 118. As drug 106 coagulates around distal piercing end 102 to form drug bolus 118, drug bolus 118 is secured to distal piercing end 102. Accordingly, needle shaft 108 may be moved within the patient to position drug bolus 118 within the patient for optimal pharmaceutical therapy, without unwanted hypodermic scratching or puncture during drug placement. Once drug bolus 118 is positioned, needle shaft 108 may be retracted from drug bolus 118 and from the patient. In one exemplary arrangement, needle shaft 108 is vibrated sufficiently to release distal piercing end 102 from drug bolus 118 and position drug bolus 118 into place in the eye. Needle shaft 108 is then retracted from the patient.

Referring to FIGS. 9-12, an exemplary arrangement of an alternative selectively expandable sleeve 10' is shown. Selectively expandable sleeve 10' is similar to that shown in FIGS. 1-8, except that sleeve 10' is constructed of a suitable material that will dissolve over a predetermined time period. Exemplary materials that may be used for sleeve 10' include, but is not limited to, glycerol ester of maleic rosin (GMR) or pentaerythritol ester of meleic rosin (PMR). In this arrangement, sleeve 10' does not include perforations. In fact, sleeve 10' serves to encapsulate drug bolus 118 within sleeve 10.' Once drug bolus 118 is created, needle housing 110 and needle shaft 108 may be retracted from sleeve 10', leaving drug bolus 118 encapsulated within sleeve 10' and positioned within the patient. The patient's own body fluids will serve to break down and dissolve sleeve 10', and permit delivery of drug 106 to the patient.

Figure 9:
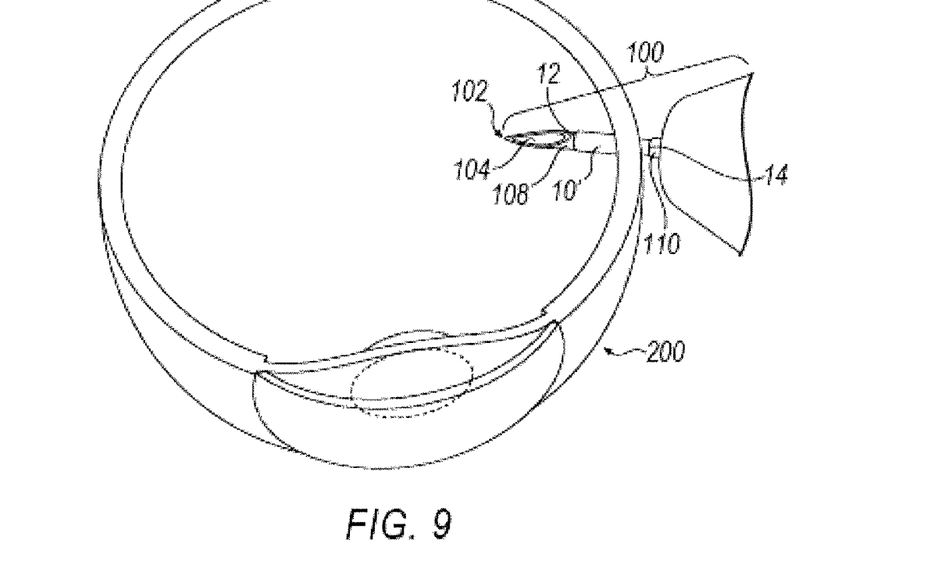
FIG. 9 illustrates an alternative arrangement of placement of a piercing element of a drug introduction tool within an eye with a selectively expandable sleeve thereon.
Figure 10:
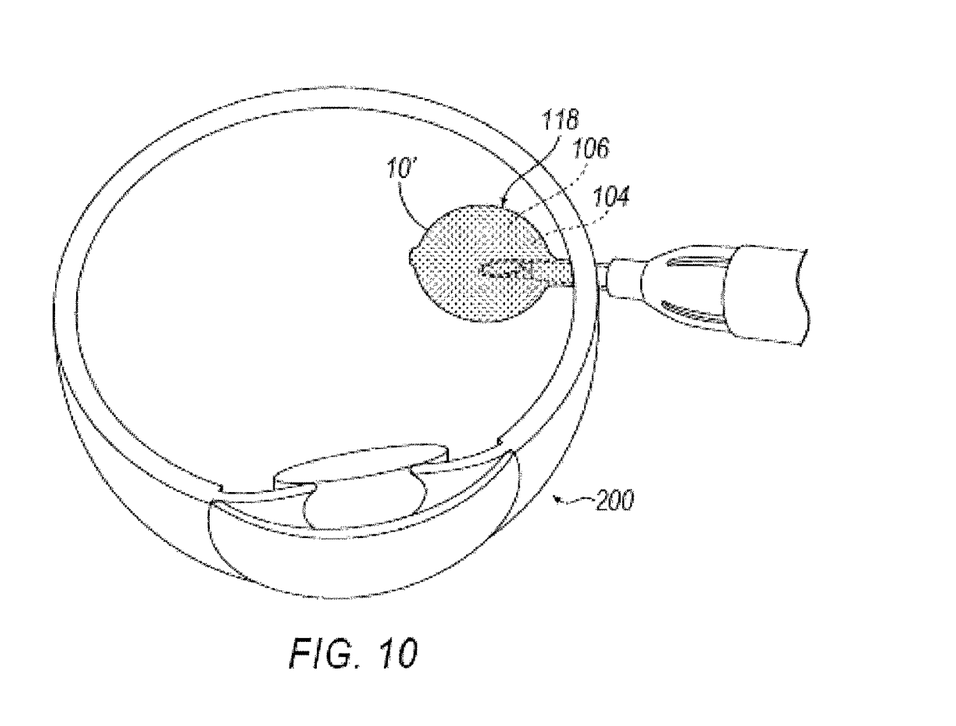
FIG. 10 illustrates the arrangement of the selectively expandable sleeve of FIG. 9 that is expanded to a predetermined volume after introduction of a suitable drug.

Referring to FIGS. 9-12, operation of selectively expandable sleeve 10' in connection with placement of drug 106 into an eye 200, will be described. As shown in FIG. 9, sleeve 10' is mounted on needle system 100 in a first unexpanded configuration. More specifically, a second end 14 is mounted on a distal end of needle housing 110. First end 12 of sleeve 10' is positioned around a portion of needle shaft 108, but is positioned proximally from distal piercing tip 102 during insertion of distal piercing tip 102 into eye 200.

Once sleeve 10' is mounted on needle system 100, distal piercing tip 102 is introduced into eye 200. Because sleeve 10' is carried by needle system 100, sleeve 10' may be introduced into eye 200 in the same introduction stroke as distal piercing tip 102. Once properly positioned within eye 200, as described above in connection with FIG. 4, distal piercing tip 102 is retracted within the interior of sleeve 10'. Phase transition drug 106 is then injected through needle shaft 108 and out of opening 104. As drug 106 is injected, sleeve 10' expands to the second expanded configuration shown in FIG. 10. Sleeve 10' serves to encapsulate drug 106 to form a drug bolus 118. Due to the properties of the phase transition drug 106, drug 106 will quickly coagulate within sleeve 10' to form drug bolus 118 before drug 106 may exit first end 12 of sleeve 10'. Because sleeve 10' encapsulates drug 106 as it is injected into eye 200, drug 106 is prevented from attaching to delicate tissues within eye 200.

Figure 11:
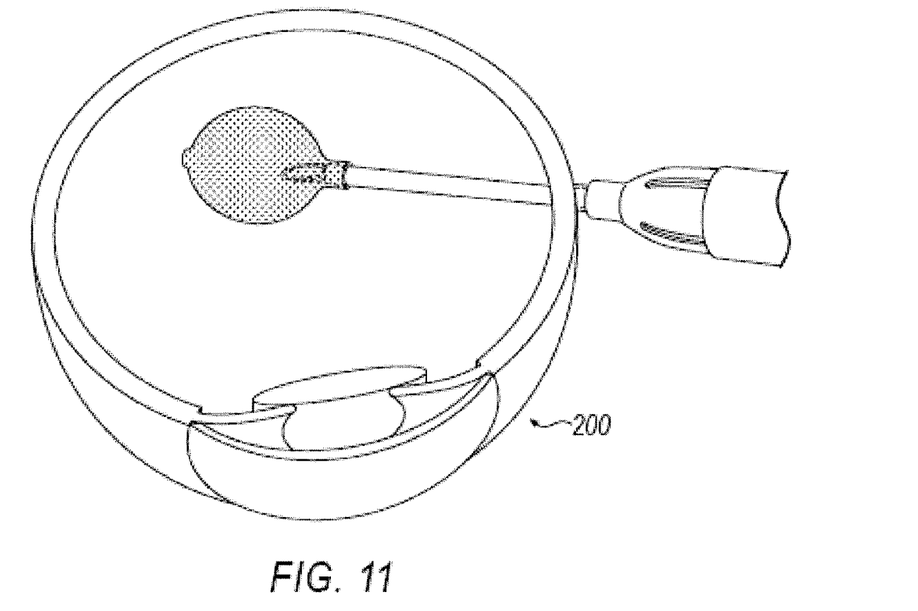
FIG. 11 illustrates selective placement of a drug bolus encapsulated within the expanded sleeve by manipulation of a portion of the drug introduction tool.
Figure 12:
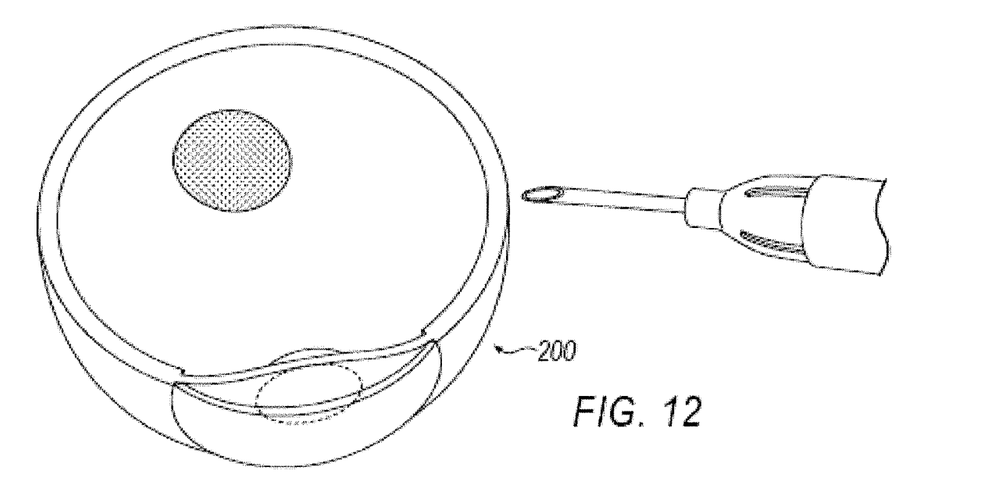
FIG. 12 illustrates extraction of the drug introduction tool and sleeve of FIG. 11 after placement of the drug bolus.

Once drug bolus 118 is formed sleeve 10' may be released from needle housing 110 and needle shaft 108. Due to the flexible and elastic nature of the material for sleeve 10', second end 14 will be twisted to a thin element and then disconnected from drug bolus 118, leaving drug bolus 118 in place within the patient. Needle housing 110 and needle shaft 108 is then retracted from the patient.

As encapsulated drug 106 coagulates around distal piercing end 102 to form drug bolus 118, drug bolus 118 is temporarily secured to distal piercing end 102. Accordingly, needle shaft 108 may be moved within the patient to position drug bolus 118 within the patient for optimal pharmaceutical therapy, without unwanted hypodermic scratching or puncture during drug placement. Once drug bolus 118 is positioned, sleeve 10' may be released from distal piercing needle 102 and needle shaft 108 may be retracted from both drug bolus 118 and from eye 200. In one exemplary arrangement, needle shaft 108 is rotated as it is retracted to release distal piercing end 102 from drug bolus 118. Alternatively, a push rod (not shown) may be inserted through needle shaft 108 to release encapsulated drug bolus 118 from distal piercing end 102. Further, needle shaft 108 may be vibrated sufficiently to loosen drug bolus 118, as described above. Once released, needle shaft 108 is retracted from eye 200.

It will be appreciated that the devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A drug introduction system, comprising:
    a selectively expandable sleeve having a body portion defined by a first open end and a second open end, wherein the body portion defines a hollow interior therein; the body portion configured to be selectively expandable from a first unexpanded configuration to a second expanded configuration whereby a volume of the hollow interior is increased when the body portion is expanded to the second expanded configuration; and
    a drug introduction tool comprising a needle housing and a needle shaft, wherein the needle shaft is mounted to the needle housing such that the needle shaft is selectively moveable with respect to the needle housing;
    wherein the needle shaft further includes a distal piercing tip having an opening therein, whereby the opening is in communication with a drug supply such that introduction of a drug causes the body portion of the sleeve to expand from the first unexpanded configuration to the second expanded configuration, sufficient to temporarily retain a drug therewithin;
    wherein the first open end of the sleeve is open to allow passage of the distal piercing tip of the needle to exit the sleeve without piercing the sleeve.

2. The drug introduction system of claim 1, wherein the body portion further comprises at least one perforation segment defined by a plurality of perforations, whereby the perforations permit the body portion to stretch along the perforation segment such that introduction of the drug into the body portion expands the body portion from the first unexpanded configuration to the second expanded configuration.

3. The drug introduction system of claim 2, further comprising a plurality of perforation segments, wherein the perforation segments are spaced equi-distance from one another.

4. The drug introduction sleeve of claim 3, wherein the second open end of the sleeve is fixedly secured to the needle housing.

5. The drug introduction system of claim 1, wherein the first open end of the sleeve is mounted around a portion of the needle shaft and the second open end of the sleeve is mounted around a portion of the needle housing.

6. The drug introduction sleeve of claim 1 wherein the first open end is defined by a first diameter and wherein the second open end is defined by a second diameter, wherein the second diameter is larger than the first diameter.

7. The drug introduction sleeve of claim 1 wherein the drug is a phase transition drug that coagulates into a drug bolus within the sleeve after dispensing from the opening of the needle shaft, wherein the drug bolus coagulates prior to exiting the first end of the sleeve such that the sleeve encapsulates the coagulated drug bolus.

8. A drug introduction system, comprising:
a selectively expandable sleeve having a body portion defined by a first open end and a second open end, wherein the body portion defines a hollow interior therein; the body portion configured to be selectively expandable from a first unexpanded configuration to a second expanded configuration whereby a volume of the hollow interior is increased when the body portion is expanded to the second expanded configuration; and
a drug introduction tool comprising a needle housing and a needle shaft, wherein the needle shaft is mounted to the needle housing such that the needle shaft is selectively moveable with respect to the needle housing;
wherein the needle shaft further includes a distal piercing tip having an opening therein, whereby the opening is in communication with a drug supply such that introduction of a drug causes the body portion of the sleeve to expand from the first unexpanded configuration to the second expanded configuration, sufficient to temporarily retain a drug therewithin;
wherein the sleeve is constructed of a material that dissolves inside an eye after a predetermined time period to release the drug into the interior of the eye.

9. The drug introduction sleeve of claim 8 wherein the first open end of the sleeve is open to allow passage of the distal piercing tip of the needle to exit the sleeve without piercing the sleeve.

10. The drug introduction sleeve of claim 8 wherein the drug is a phase transition drug that coagulates into a drug bolus within the sleeve after dispensing from the opening of the needle shaft.

11. The drug introduction system of claim 8, wherein the body portion further comprises at least one perforation segment defined by a plurality of perforations, whereby the perforations permit the body portion to stretch along the perforation segment such that introduction of the drug into the body portion expands the body portion from the first unexpanded configuration to the second expanded configuration.

12. The drug introduction system of claim 11, further comprising a plurality of perforation segments, wherein the perforation segments are spaced equi-distance from one another.

13. The drug introduction system of claim 8, wherein the first open end of the sleeve is mounted around a portion of the needle shaft and the second open end of the sleeve is mounted around a portion of the needle housing.

14. The drug introduction sleeve of claim 8 wherein the first open end is defined by a first diameter and wherein the second open end is defined by a second diameter, wherein the second diameter is larger than the first diameter.

15. A drug introduction system, comprising:
a selectively expandable sleeve having a body portion defined by a first open end and a second open end, wherein the body portion defines a hollow interior therein; the body portion configured to be selectively expandable from a first unexpanded configuration to a second expanded configuration whereby a volume of the hollow interior is increased when the body portion is expanded to the second expanded configuration; and
a drug introduction tool comprising a needle housing and a needle shaft, wherein the needle shaft is mounted to the needle housing such that the needle shaft is selectively moveable with respect to the needle housing;
wherein the needle shaft further includes a distal piercing tip having an opening therein, whereby the opening is in communication with a drug supply such that introduction of a drug causes the body portion of the sleeve to expand from the first unexpanded configuration to the second expanded configuration, sufficient to temporarily retain a drug therewithin;
wherein the drug is a phase transition drug that coagulates into a drug bolus within the sleeve after dispensing from the opening of the needle shaft, wherein the drug bolus coagulates prior to exiting the first end of the sleeve such that the sleeve encapsulates the coagulated drug bolus.

16. The drug introduction system of claim 15, wherein the body portion further comprises at least one perforation segment defined by a plurality of perforations, whereby the perforations permit the body portion to stretch along the perforation segment such that introduction of the drug into the body portion expands the body portion from the first unexpanded configuration to the second expanded configuration.

17. The drug introduction system of claim 16, further comprising a plurality of perforation segments, wherein the perforation segments are spaced equi-distance from one another.

18. The drug introduction system of claim 15, wherein the first open end of the sleeve is mounted around a portion of the needle shaft and the second open end of the sleeve is mounted around a portion of the needle housing.

19. The drug introduction sleeve of claim 15 wherein the first open end is defined by a first diameter and wherein the second open end is defined by a second diameter, wherein the second diameter is larger than the first diameter.

20. The drug introduction sleeve of claim 15 wherein the first open end of the sleeve is open to allow passage of the distal piercing tip of the needle to exit the sleeve without piercing the sleeve.

* * * * *